United States Patent
Andersson et al.

(10) Patent No.: US 11,992,704 B2
(45) Date of Patent: May 28, 2024

(54) METHOD, COMPUTER PROGRAM PRODUCT AND COMPUTER SYSTEM FOR PARTICLE-BASED RADIOTHERAPY TREATMENT PLANNING

(71) Applicant: RaySearch Laboratories AB, Stockholm (SE)

(72) Inventors: Bjorn Andersson, Uppsala (SE); Cecilia Battinelli, Stockholm (SE); Rasmus Bokrantz, Enebyberg (SE)

(73) Assignee: Raysearch Laboratories AB (publ), Stockholm (SE)

( * ) Notice: Subject to any disclaimer, the term of this patent is extended or adjusted under 35 U.S.C. 154(b) by 305 days.

(21) Appl. No.: 17/596,506

(22) PCT Filed: Jun. 2, 2020

(86) PCT No.: PCT/EP2020/065169
§ 371 (c)(1),
(2) Date: Dec. 11, 2021

(87) PCT Pub. No.: WO2020/249418
PCT Pub. Date: Dec. 17, 2020

(65) Prior Publication Data
US 2022/0233883 A1  Jul. 28, 2022

(30) Foreign Application Priority Data
Jun. 12, 2019 (EP) .................................... 19179757

(51) Int. Cl.
*A61N 5/10* (2006.01)
(52) U.S. Cl.
CPC .... *A61N 5/1031* (2013.01); *A61N 2005/1087* (2013.01)

(58) Field of Classification Search
CPC .... A61N 2005/1041; A61N 1/02; A61N 5/00; A61N 5/10; A61N 5/103; A61N 5/1031;
(Continued)

(56) References Cited

U.S. PATENT DOCUMENTS

| 2010/0327188 A1 | 12/2010 | Bert et al. |
| 2015/0217135 A1 | 8/2015 | Bohsung et al. |
| 2019/0091488 A1 | 3/2019 | Ding et al. |

FOREIGN PATENT DOCUMENTS

WO  WO-2017156419 A1 * 9/2017 ............. A61N 5/103

OTHER PUBLICATIONS

International Search Report. International application No. PCT/EP2020/065169. Patent Cooperation Treaty. European Patent Office, P.B. 5818 Patentlaan 2, NL—2280 HV Rijswijk. the international search report: dated Mar. 7, 2020. pp. 1-5.

(Continued)

*Primary Examiner* — Don K Wong
(74) *Attorney, Agent, or Firm* — Noréns Patentbyrå AB

(57) ABSTRACT

A method of radiotherapy treatment planning for particle-based arc treatment comprises the steps of
determining (S11; S21) an initial set of candidate energy layers,
performing a calculation on the initial set,
determining (S13; S23), based on the outcome of said calculation, at least one additional energy layer to produce an expanded candidate layer set, wherein the at least one additional energy layer involves an energy level that has not previously been used
adding (S14; S24) the at least one additional energy to the initial set, to produce an expanded candidate energy layer set
optimizing (S16; S26) a radiotherapy treatment plan based on the expanded candidate layer set.

11 Claims, 1 Drawing Sheet

(58) Field of Classification Search
CPC .. A61N 5/1038; A61N 5/1042; A61N 5/1048; A61N 5/1043; A61N 5/1044; A61N 5/1071; A61N 5/1064; A61N 2005/1087; G01T 1/02
See application file for complete search history.

(56) References Cited

OTHER PUBLICATIONS

Written Opinion of the International Searching Authority. International application No. PCT/EP2020!065169. Filing date: Feb. 6, 2020. Patent Cooperation Treaty. European Patent Office, D-80298 Munich. dated Mar. 7, 2020. pp. 1-5.

* cited by examiner

METHOD, COMPUTER PROGRAM PRODUCT AND COMPUTER SYSTEM FOR PARTICLE-BASED RADIOTHERAPY TREATMENT PLANNING

TECHNICAL FIELD

The present invention relates to a system and a method for particle-based radiotherapy treatment planning and delivery in particular to the planning of arc treatment.

BACKGROUND

In particle-based radiotherapy treatment, patients are irradiated with charged particles such as protons. The particles are controlled in such a way that they will deposit most of their energy at specific depths in the patient so that the whole target will be covered. At the same time, some energy will be deposited along the path towards the target. Each particle will deposit most of its energy towards the end of its path, in what is known as the Bragg peak. The depth of the Bragg peak in the patient can be controlled by adjusting the kinetic energy of the particles. The lateral position of the Bragg peak can be controlled using electromagnets to deflect the focused beam. This allows for the delivery of highly localized doses at well-controlled positions in the patient. The dose delivered from a certain combination of kinetic energy, and lateral deflection of the beam is referred to as a spot. The number of particles delivered to a spot is commonly referred to as the spot weight. By providing spots in many different locations in a three-dimensional space, the target volume can be fully covered with the desired dose distribution. This procedure is called active scanning ion beam therapy, also known as pencil beam scanning.

The kinetic energies of the spots are often, but not necessarily, distributed over a number of discrete energies. A group of spots with the same kinetic energy, but different lateral deflection is often referred to as an energy layer. To cover a desired volume in a patient, different energy layers are defined such that particles of a particular energy layer will deposit their energy at a certain depth in the patient. The energy layers are selected in such a way that the Bragg peaks will be distributed over the volume to be treated.

The spot weights of all energy layers are determined in the treatment planning system through optimization, and the spot weights are iteratively varied to achieve desired objectives or constraints related to dose levels or other relevant quantities. The case where the spot weights are allowed to vary freely over the beams is referred to as intensity-modulated proton therapy (IMPT).

Proton arc therapy involves radiation in a sequence of a large number of beams from different angles, for example 10 or more, 50 or more, or 100 or more angles, each having a number of energy layers, for example up to 20 energy layers. The adjustment between each energy layer, and between each angle, takes time. The arc can be delivered either as multiple separate beams or through a continuous moving arc. In the latter case, the beams will serve as control points as is known from photon arc therapy. Hereinafter, the terms beam, beam direction or beam angle could equally well be substituted by the term control point, if the arc is continuous. The term energy layer in this document refers to a specific energy level in a specific beam. If the same energy level is used in two beams, this will be considered to constitute two separate energy layers.

The selection of energy layers, including the selection of beam angles, for the whole arc is crucial for achieving a high-quality plan. A high number of energy layers will often enable a higher plan quality but will also increase the delivery time to the patient and thereby the cost of the resulting plan in terms of the risk of patient movement within a fraction, patient discomfort during treatment, but also clinical efficiency and economic considerations. There is always a desire to reduce delivery time, while still maintaining a high-quality plan which will ensure effective treatment of the patient. Treatment planning should therefore strive for a selection of energy layers that will enable a high-quality plan with a limited set of energy layers.

Published US patent application No. 2019/0091488 proposes an iterative method for proton arc therapy including, in each iteration, control point resampling, energy layer redistribution, energy layer filtration, and energy layer resampling. Each control point corresponds to a beam angle. A small number of control points are defined, each with a number of energy layers, and the plan is optimized. After optimization, one control point is selected at random, is split and replaced with a pair of adjacent sub-control points, located, for example 5 degrees to either side of the original control point. The energy layers of the original control point are either copied to both sub-control points or split between the sub-control points, before optimizing the plan again. Because the sub-control points are located at a small angle from the original control point, it is assumed that the same energy levels should be used. This may be repeated a number of times, so that also a sub-control point may be divided and replaced by two adjacent control points having all or a subset of the same energy layers. Spots and/or energy layers having a low weight may subsequently be filtered out by conventional spot or energy layer filtering methods.

Co-pending European application No. 18165472.4 discloses a treatment planning method for particle-based arc treatment, starting with a set of energy layers, in which the number of energy layers included in the plan may be reduced as part of the optimization step by including in the optimization problem a penalty designed to limit the number of energy layers. This allows the optimization of the number of energy layers, and their positions in the same operation as optimizing the treatment plan. The method only chooses between energy layers already in the set and does not foresee the addition of energy layers.

SUMMARY

It is an object of the present invention to provide a set of energy layers on which to base arc radiotherapy treatment planning, which will provide a high quality treatment plan while also minimizing the computational effort required.

This object is achieved according to the present invention by a method of radiotherapy treatment planning for creating a plan for delivery of at least one particle-based arc to a patient using an apparatus arranged to deliver radiation in the form of charged particles from a number of different directions, the method comprising the steps of
  a. determining an initial set of candidate energy layers, each layer involving a particular energy level at a particular beam angle,
  b. performing a calculation on the initial set,
  c. determining, based on the outcome of said calculation, at least one additional energy layer to produce an expanded candidate layer set, wherein the at least one additional energy layer involves an energy level not previously used in any of the energy layers,
  d. adding the at least one additional energy to the initial set, to produce an expanded candidate energy layer set e. optimizing a radiotherapy treatment plan based on the expanded candidate layer set.

According to the present invention, therefore, the candidate set of energy layers may be expanded by adding energy layers that will make a significant contribution to the resulting plan. Which energy layers to add is determined based on the result of plan optimization or dose calculation. For example, energy layers may be added in regions in which a lot of energy is deposited, where it seems that another energy layer would be useful. Alternatively, or in addition, energy layers may be added to produce spots in regions lacking coverage, to improve the coverage. Importantly, energy levels not previously used by any of the energy layers may be used, so that one or more of the energy layers that are added will have an energy level that has not previously been used by any of the energy layers. An energy layer having a previously unused energy level may be added to an existing beam angle or for a newly added beam angle.

In one embodiment, the calculation involves a dose calculation and the determining at least one additional energy layer is based on the result of the dose calculation, for example identifying a region in which the Bragg peak density is low and the additional energy layer is determined to provide a Bragg peak in that area. This involves limited calculating efforts and in particular enables the addition of new energy layers without first performing an optimization.

In a preferred embodiment, the calculation involves a treatment plan optimization based on an optimization problem and the determining at least one additional energy layer is based on the resulting treatment plan. The optimization requires more computational power but also yields a better basis for determining the new energy layers in the best possible way.

In preferred embodiments, the energy layer expansion method is combined with method steps for discarding energy layers. One such method involves optimizing the plan using an optimization problem formulation designed to produce a suitable dose distribution, in such a way that the plan will use only subsets of beam angles and energy layers from the set of beam angles and the set of energy layers, respectively. This may be done using a greedy or reverse-greedy method, both of which start with a candidate set of energy layers. In a reverse-greedy method the full candidate set is included from the start, and layers are discarded according to a score based on their spot weights and/or their gradients. After a first optimization the layers to be discarded are determined. For example, the n layers having the lowest score are discarded, n being an integer, for example 10% of the candidate set. Alternatively, all layers having a score below a threshold value may be discarded. The optimization is then repeated and the m layers having the lowest sum of spot weights are discarded, m being an integer equal t or different from n. This may be repeated again until a specific number of energy layers remain. A combination of the greedy and reverse greedy approaches may be used, by first using a greedy method to generate a subset and then refining the subset using a reverse greedy method.

In a greedy method, the first optimization is based on a subset of the candidate set. A score, based on gradient based points, is determined. Based on the score, layers in the candidate set that are not included in the subset may be added to the subset and a new optimization may be performed. For example, a fixed number of layers may be added, or all layers having a score above a certain threshold value may be added. This may be repeated until the specific number of energy layers has been reached. In both the greedy and the reverse greedy method the optimization may be repeated for example until a predetermined number of energy layers or a certain fraction of the candidate set remains, or until all remaining energy layers have a spot weight sum above a threshold value. The energy layer discarding step in the reverse greedy method, and the energy layer including step in the greedy method, may be defined to act on the entire arc or on one or more sub-sets of the arc, each sub-set comprising one or more beams.

In preferred embodiments, the optimization is subject to a penalty designed to limit the number of energy layers. This will ensure that the best energy layers, that is, the ones that contribute most effectively to the dose are kept while energy layers resulting in low doses are discarded.

The penalty may be defined as one or more constraints or terms in an objective function used in the optimization, or a combination of the two.

The penalty may be expressed in terms of the number of energy layers. Minimizing the number of energy layers used reduces the plan delivery time because changing between different energy layers is time consuming. Alternatively, the penalty may be expressed in terms of the number of energy layer changes between adjacent angles. This will enable, for example, keeping the energy layer when changing beam angles, thus saving time. It is also possible to express the penalty in terms of both the number of energy layers and the number of energy layer changes.

The penalty may be defined to act on the entire arc or on one or more sub-sets of the arc, each sub-set comprising one or more beams.

The invention also relates to a computer program product for controlling a radiotherapy planning apparatus, preferably stored on a carrier such as a non-transitory storage means, said computer program product comprising computer readable code means which when run in a processor of a radiotherapy planning apparatus will cause the apparatus to perform the method as discussed above.

The invention also relates to a radiotherapy treatment planning apparatus comprising a processor and a program memory holding a computer program product according to the above, arranged to be run in the processor to control the radiotherapy treatment planning apparatus.

BRIEF DESCRIPTION OF THE DRAWINGS

The invention will be described in more detail in the following, by way of example and with reference to the appended drawings, in which.

DETAILED DESCRIPTION

The method according to the invention is based on a candidate set of energy layers that can be expanded according to certain criteria.

Figure 1:
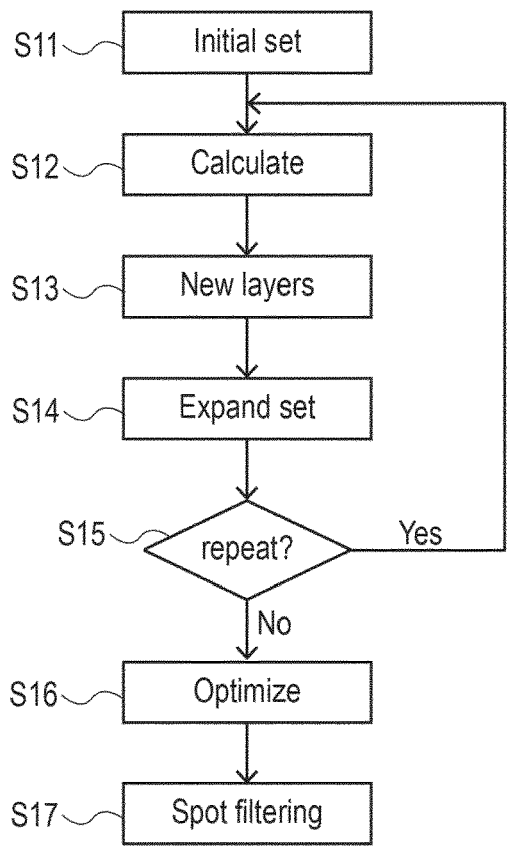
FIG. 1 is a flow chart of a first embodiment of the method according to invention

In the simplest form, the method may be as shown in FIG. 1. In a first step S11, an initial set of energy layers is obtained. As discussed above, an energy layer is an energy level associated with a particular beam angle. In this embodiment the initial set should preferably be small enough that the initial dose calculation or optimization can be done within a reasonable time frame. The set may consist of, for example one or a few beam angles, each having a few energy layers. Next, in step S12, a calculation, for example, a treatment plan optimization is performed based on the initial set. In step S13 the result of the calculation is used to determine at least one additional energy layer, in a new beam angle or in a beam angle already included in the initial set. The initial set of energy layers is then expanded in step S14 by adding the energy layer or layers from step S13 to create an expanded set. The energy layers may be added for an existing beam angle and/or one or more new beam angles may be selected. This may be repeated one or more times, by treating the expanded set as an initial set to be expanded again and returning to step S11.

In one embodiment, the calculation in step S12 involves a treatment plan optimization. In that case, information from the resulting treatment plan may be used to determine the additional energy layers in step S13. In other embodiments, step S12 instead involves a simpler calculation, such as a dose calculation for each energy layer in the initial set. In step S13 in the latter case, the additional energy layer or layers are determined based on the resulting doses calculated for each energy layer. This will provide less information than a treatment plan optimization but still provide information such as Bragg peak positions, that may be used to determine the additional energy layers. For example, regions where the density of Bragg peaks is low may be identified and the additional energy layers may be determined so that new Bragg peaks will be created in these regions, to ensure an appropriate Bragg peak density across the target.

Step S15 is a decision step to decide if another expansion of the energy layer set should be performed. If yes, return to step S12 performing the calculation of step S12 on the expanded set. If no, perform an optimization in step S16 based on the expanded set to obtain an arc treatment plan. Step S17 is an optional step in which spots having low spot weights are filtered. Spot filtering can be performed both to increase the treatment efficiency, but also because the machine may have a physical limitation of how small spot weights it is able to deliver. Typically, the spots are also sorted, that is, the order in which they are to be irradiated is determined to minimize the time required. Spot filtering and spot sorting are known procedures, which may be performed at any suitable point in the procedure.

In all embodiments, the selection in step S13, and in step S23 below, should be performed in such a way as to add energy layers that are likely to be useful in the plan, that is, energy layers that will make a significant contribution to the total dose. In practice, several different criteria can be applied to achieve this.

For example, new energy layers may be added near energy layers that result in high spot weights in a resulting treatment plan. Alternatively, or in addition, the geometry of the Bragg peak positions may be considered so that new energy layers are added that will result in new Bragg peaks in regions in which the density of Bragg peaks is low. A further criterion may be that if there is a high amount of radiation from one beam angle, or a group of adjacent beam angles, new energy levels should be added in the vicinity of those beam angles, preferably in the form of new beam angles, each having a number of energy layers. New energy layers may also be added near energy layers having a high weight, in the same beam, to increase the energy level density within a beam. The beam angles and energy layers may be selected on the basis of what will make the most useful contribution to the total dose, independently of the beam angles and energy levels of existing energy layers, in the sense that new energy layers can be added exactly as is seen fit, with the possibility to use new energy levels not used originally. This means that for an existing beam angle, one or more energy layers can be added where they are deemed to be useful, without any regard to existing energy layers in this or other beams. For a new beam angle, the energy layers will be selected as the optimal ones for this new beam angle, without any regard to the energy layers of any existing beam angle.

After the desired number of iterations, the resulting expanded set will be used in an optimization step for treatment planning.

There may be a predefined candidate set of possible energy layers, including possible beam angles, that may be selected for addition to the initial set of energy layers, or it may be possible to define new beam angles and associated energy layers freely.

Preferably, the method also includes ways of reducing the number of energy layers to ensure that energy layers that are not important for the plan are discarded. This typically means removing energy layers that contribute very little to the overall dose, which enables the computational effort to be reduced with a minimum effect on the plan quality. This could be done by a simple method such as energy layer filtering, in which energy layers for which the sum of the layer's spot weights is low are filtered out. According to preferred embodiments, this is achieved by an optimization problem that includes a penalty designed to reduce the number of energy layers.

Figure 2:
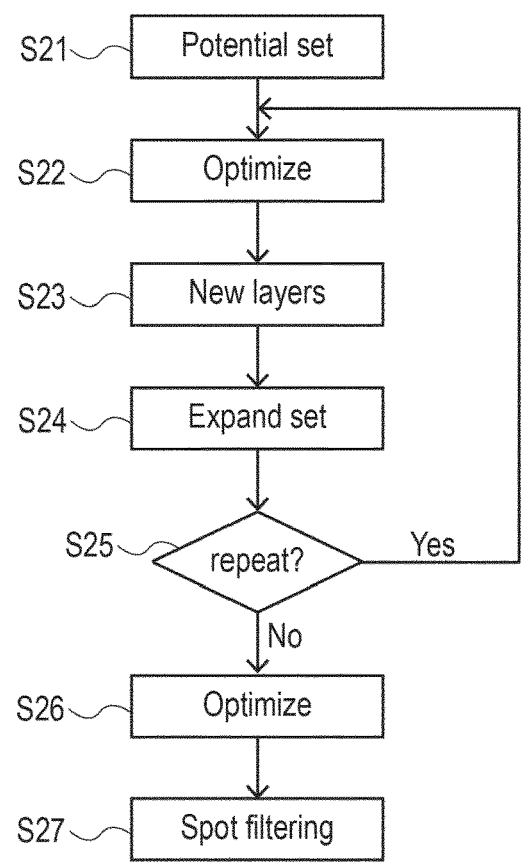
FIG. 2 is a flow chart of a second embodiment of the method according to invention

FIG. 2 illustrates such an embodiment, in which a sequence of expansions and reductions of the set of energy layer is performed iteratively.

In a first step S21 a set of potential energy layers is defined. For pencil beam scanning treatment methods, a set of spots for each layer is also defined. This may involve obtaining an arc trajectory and specifying a number of beam angles for the arc, and energy layers associated with each beam angle.

In the next step S22, an optimization is performed, in which the treatment plan is optimized based on the set of potential energy layers defined in step S21. In the optimization problem, one or more penalties are set on the number of energy layers, and/or the number of energy layer changes, and/or on the number of beams. In the following, the singular form "penalty" is used, but it should be understood that a number of penalties may be applied together. More detail about this step is provided below. This optimization will result in a reduced set of energy layers, which may be used as an initial set of energy layers in the method of FIG. 1, or for creating the expanded set as described in the following.

In the following steps, the reduced set of energy layers from step S22 is expanded to create an expanded set. In step S23 the result of the treatment plan optimization in step S22 is used to determine at least one additional energy layer, in a new beam angle or in a beam angle already included in the initial set. The initial set of energy layers is then expanded in step S24 by adding the energy layer or layers from step S23 to create an expanded set. The energy layers may be added for an existing beam angle and/or one or more new beam angles may be selected.

Step S25 is a decision step to decide if another expansion of the energy layer set should be performed. If yes, return to step S22 performing the optimization of step S22 using the expanded set as the new potential set. If no, perform an optimization in step S26 based on the expanded set an using the same type of optimization problem as discussed for step S22, to obtain an arc treatment plan. Step S27 is an optional step in which energy layers having low spot weights are filtered out in a conventional manner. As for the procedure of FIG. 1, spot filtering and spot sorting may be performed at any suitable point in the procedure.

In the steps S22 and S26, the optimization is performed using an optimization problem including a penalty designed to reduce the number of energy layers. The penalty may be defined as a constraint, setting an absolute limit, or as terms in the objective function, reflecting a desire to limit the number of energy layers as much as possible. The penalty may be defined in terms of limiting the number of energy layers, of limiting the number of changes of energy layer during the treatment, or in any other suitable way that will ensure that the optimization algorithm will systematically reduce the time that will have to be spent changing between energy layers during treatment delivery. In step S22, the optimization may start with the full initial set of beam angles and energy layers, so that the optimization process will reduce the number of beam angles and energy layers by removing the ones that make the smallest contributions to the plan. When an energy layer is removed, the spot weights of that layer may be distributed to the remaining energy layers, in order to minimize the perturbation to the solution caused by the removal of the layer. How to do this is known in the art and may involve constructing a three-dimensional Delaunay triangulation of the Bragg peaks of the remaining layers and distributing the weight of each spot to be removed in accordance to its position in the triangulation. Alternatively, the optimization may start with no beam angles and energy layers and the optimization process will proceed to add the ones that make the most useful contributions to the plan. In both cases, the beam angles and energy layers considered are the ones from the sets defined in steps S21. Some more specific examples of both types of optimization methods will be discussed below.

The penalty may be set to act on the entire arc, limiting the number of energy layers per arc to a maximum value. Alternatively, the penalty may be set to act on each angle individually, to set a maximum number of energy layers per beam. As a third option, sub-arcs, each containing a subset of the arc, could be defined and the penalty may be set to limit the number of energy layers for each sub-arc. The same applies if the penalty is set in terms of an objective function. A sub-arc could comprise any suitable number of consecutive beams, for example, three or five, but a sub-arc could also comprise only one beam. In particular, if the penalty is specified to limit the number of energy layer changes, it will be suitable to set the penalty to the whole arc or to sub-arcs comprising more than one angle. This is because in this case such a penalty can avoid changing the energy layer between two beams by using the last energy layer in one beam as the first energy layer in the next beam.

The energy layer selection penalty can be formulated mathematically by introduction of a function $y: R^m \rightarrow R^n$ that maps vectors of spot weights $x \in R^m$ (defined across all energy layers and angles) to some measure of how much each energy layer at each angle is used. The component functions $y_1, \ldots, y_n$ may preferably be defined such that that $y_i(x)$ is positive if the combination of energy layer and angle at index i has any spot with positive weight, and zero otherwise. One possible formulation of a component function $y_i$ is as a norm $\|x^i\|$ of a sub-vector $x^i$ that is associated with some energy layer and angle. A penalty on the maximum number of energy layers per arc may with this notation be expressed as $card(y) \leq b$, where the cardinality operator $card(\cdot)$ denotes the number of non-zero entries of a vector. Constraints on sub-arcs or individual angles are similarly formulated with respect to sub-vectors of y. The penalties will be referred to in the following as cardinality penalties. The penalty term in the optimization function is based on a continuous approximation method.

Such methods will start from the complete set of beams and energy layers and remove some during optimization. The cardinality operator is here approximated by a continuous function, which removes the combinatorial aspect of the problem. The resulting approximate problem can be solved by some method for continuous optimization, such as an interior-point method or a sequential quadratic programming method. One possible reformulation of a problem with cardinality penalties into continuous problem is to express the cardinality operator as a sum of step functions s according to $card(y) = \Sigma_i s(y_i)$, where s evaluates to zero for non-positive numbers and one otherwise, and then substitute a continuous but approximate step function for the exact function s. Examples of functions that could be used to approximate s are the logistic function or the error function, or simply the positive part function. The method could be applied in steps, so that multiple optimizations are performed and the accuracy of the approximation of the step function is increased between optimizations until the result is acceptable considering the cardinality penalty. If the cardinality penalty is formulated as a constraint, this means that the constraint is fulfilled. If the cardinality penalty is formulated as a term in the objective function, the term is minimized.

The objective functions and constraints in the optimization problem should be able to optimize on different quantities, most importantly dose and LET-related quantities, such as LET and dose-weighted LET. The LET (Linear Energy Transfer) could more efficiently be focused inside the target using proton arcs than in normal IMPT, if considered in the optimization.

At any point of the optimization procedure, typically at the end, as indicated by steps S17 and S27, spot filtering may be applied to filter out spots that have a low weight assigned to them. Preferably the weight of these filtered-out spots is reassigned to other spots that are kept in the plan. Several methods of doing this are known in the art and they will not be discussed here in any detail.

If the number of spots in the initial set of energy layers is so large that it is not feasible to calculate and store the doses for all the spots, it is possible to preprocess it to remove some of the energy levels before starting the procedure according to the invention. This may be done in any suitable way. For example, for two adjacent beam angles having the same or similar energy levels, some energy levels could be removed from each of the beam angles, in such a way that the ones that were removed from one were kept in the other and vice versa. The pre-processing method may remove energy layers in a uniform fashion until the candidate set is small enough to allow numerical calculations. It may also be based on some rule, such a preference for distal layers over proximal layers. The pre-processing could also be based on Bragg peak positions, if an approximate and inexpensive technique to calculate Bragg peak positions from spot positions and energies is available. For such a method, the pre-processing may remove energy layers in a way that strives to maintain a uniform spread of Bragg peaks over the target volume.

Figure 3:
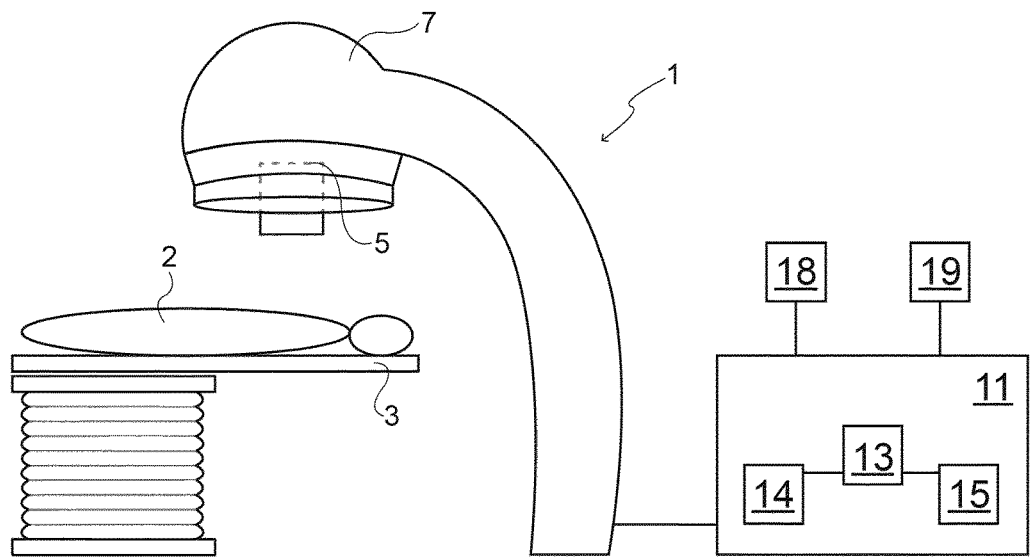
FIG. 3 illustrates schematically a system in which the invention may be implemented.

FIG. 3 is an overview of a system for radiotherapy treatment imaging and/or planning, adapted to provide radiation to a patient from different directions. As will be understood, such systems may be designed in any suitable way and the design shown in FIG. 3 is only an example. A patient 11 is positioned on a treatment couch 13. The system comprises a treatment unit 10 having a radiation source 15 mounted in a gantry 17 for emitting radiation towards the patient positioned on the couch 13. Typically, the couch 13 and the gantry 17 are movable in several dimensions relative to each other, to provide radiation to the patient as flexibly and correctly as possible. In particular, the gantry can rotate around the couch, either between certain angles or a full 360° rotation. Alternatively, the gantry can be fixed and the couch carrying the patient can rotate instead. Another alternative is to have the patient in seated position in a chair. The arc treatment in this case could be performed by changing the beam directions or rotating the chair. These parts are well known to the skilled person. The system also comprises a computer 21 which may be used for radiotherapy treatment planning and/or for controlling radiotherapy treatment. As will be understood, the computer 21 may be a separate unit not connected to the imaging unit.

The computer 21 comprises a processor 23, a data memory 24, and a program memory 26. Preferably, one or more user input means 28, 29 are also present, in the form of a keyboard, a mouse, a joystick, voice recognition means or any other available user input means. The user input means may also be arranged to receive data from an external memory unit.

The data memory 24 comprises clinical data and/or other information used to obtain a treatment plan, including a set of clinical goals to be used for planning. The data memory 24 also comprises one or more dose maps for one or more patients to be used in treatment planning according to embodiments of the invention. The program memory 26 holds a computer program, known per se, arranged for treatment plan optimization. The program memory 26 also holds a computer program arranged to make the computer control the treatment of a patient in accordance with the invention.

As will be understood, the data memory 24 and the program memory 26 are shown and discussed only schematically. There may be several data memory units, each holding one or more different types of data, or one data memory holding all data in a suitably structured way, and the same holds for the program memories. One or more memories may also be stored on other computers. For example, the computer may only be arranged to perform one of the methods, there being another computer for performing the optimization.

To reduce the damage to surrounding tissue further, the described optimization method could be combined with an approach where the plan is set up of similar arcs delivered on different treatment fractions delivered on different days. The different arcs include different beam angles, so that the target is covered in the same way, but the way through the patient to the tumor is different for different fractions.

Radiotherapy using charged particles such as protons enables the optimization of highly precise plans. This in turn means that small errors, for example in the setup, can have large consequences for the delivered dose. Therefore, the optimization method used according to the invention should preferably be a robust optimization method. This becomes even more important when the number of energy layers are reduced. The method should be robust with respect to different uncertainties to ensure that plan quality is preserved even when there are uncertainties in the delivery (e.g. range and setup uncertainties). As an alternative to robust optimization methods, a method aiming at creating uniform doses for each angle (compare SFUD (Single Field Uniform Dose) in normal active scanning plan optimization) or for each set of angles (each sub arc) would be suitable. If a low number of energy layers per angle is desired, the most feasible solution is to aim at uniform doses for each sub arc.

The described methods could be employed for all types of active scanning, including spot scanning, raster scanning, and line scanning. Implementation of line scanning in conjunction with proton arc therapy would be beneficial in terms of delivery time. The methods are suitable for planning treatment of humans, but also of small animals, such as mice, for preclinical trials. The described methods work equally well for other light ions than protons, such as helium, carbon and oxygen, as long as the different biological effects of different ion types are accounted for in biological (RBE) models included in the optimization process.

The invention claimed is:

1. A method of radiotherapy treatment planning for creating a plan for delivery of at least one particle-based arc to a patient using an apparatus arranged to deliver radiation in the form of charged particles from a number of different directions comprising the steps of
   a. determining (S11; S21) an initial set of candidate energy layers, each layer involving a particular energy level at a particular beam angle,
   b. performing a calculation on the initial set,
   c. determining (S13; S23), based on the outcome of said calculation, at least one additional energy layer to produce an expanded candidate layer set, wherein the at least one additional energy layer involves an energy level not previously used in any of the energy layers,
   d. adding (S14; S24) the at least one additional energy layer to the initial set, to produce an expanded candidate energy layer set
   e. optimizing (S16; S26) a radiotherapy treatment plan based on the expanded candidate layer set.

2. A method according to claim 1, wherein the calculation involves a dose calculation and the determining at least one additional energy layer is based on the result of the dose calculation, for example identifying a region in which the Bragg peak density is low and the additional energy layer is determined to provide a Bragg peak in that area.

3. A method according to claim 1, wherein the calculation involves a treatment plan optimization based on an optimization problem and the determining at least one additional energy layer is based on the resulting treatment plan.

4. A method according to claim 3, wherein the optimization (S22, S26) is performed based on an optimization problem formulation designed to produce a suitable dose distribution, in such a way that the plan will use only a subset of beam angles and/or a subset of energy layers from the set of beam angles and the set of energy layers, respectively.

5. A method according to claim 4, wherein a potential set of energy layers is provided and the optimization includes a first optimization procedure based on the whole potential set, and a subsequent step of discarding a some of the energy layers from the potential set based on their spot weights and/or gradients, to create a reduced potential set and performing a second optimization procedure (S26) based on the reduced potential set.

6. A method according to claim 4, wherein a potential set of energy layers is provided, and the optimization includes a first optimization procedure based on a first subset of the potential set, and a subsequent step of adding some of the energy layers from the potential set not included in the subset to the subset based on a calculation of the gradient of the spot weights with respect to the optimization objective to create an expanded subset, and performing a second optimization procedure based on the expanded subset.

7. A method according to claim 4, wherein the optimization is designed to limit the number of energy layers.

8. A method according to claim 7, wherein the limitation of the energy layers is achieved by means of a penalty implemented as a constraint or a term in an objective function used in the optimization.

9. A method according to claim 8, wherein the limitation of the energy layers is achieved by means of a penalty expressed in terms of the number of energy layers or the number of energy layer changes.

10. A computer program product for controlling a radiotherapy planning apparatus, preferably stored on a carrier such as a non-transitory storage means, said computer program product comprising computer readable code means which when run in a processor of a radiotherapy planning apparatus will cause the apparatus to perform the method according to claim 1.

11. A radiotherapy treatment planning apparatus (10) comprising a processor (23) and a program memory (26) holding a computer program product according to claim 10, arranged to be run in the processor to control the radiotherapy treatment planning apparatus.

* * * * *